(12) United States Patent
Gines

(10) Patent No.: US 6,228,080 B1
(45) Date of Patent: *May 8, 2001

(54) ELECTROSURGICAL GENERATOR WITH ADAPTIVE POWER CONTROL

(75) Inventor: David Lee Gines, Boulder, CO (US)

(73) Assignee: Sherwood Services AG, Schaffhausen (CH)

(*) Notice: Subject to any disclaimer, the term of this patent is extended or adjusted under 35 U.S.C. 154(b) by 0 days.

This patent is subject to a terminal disclaimer.

(21) Appl. No.: 09/209,323

(22) Filed: Dec. 11, 1998

Related U.S. Application Data

(63) Continuation of application No. 08/838,548, filed on Apr. 9, 1997, now Pat. No. 6,033,399.

(51) Int. Cl.$^7$ .................................................. A61B 18/18
(52) U.S. Cl. .................................................. 606/34; 606/42
(58) Field of Search .................... 606/32–34, 37–42

(56) References Cited

U.S. PATENT DOCUMENTS

| | | |
|---|---|---|
| 3,875,945 | 4/1975 | Friedman . |
| 4,092,986 | 6/1978 | Schneiderman . |
| 4,191,188 | 3/1980 | Belt et al. . |
| 4,378,801 | 4/1983 | Oosten . |
| 5,438,302 | 8/1995 | Goble . |
| 5,451,224 | 9/1995 | Goble et al. . |
| 5,472,443 * | 12/1995 | Cordis et al. .......................... 606/48 |
| 5,496,312 * | 3/1996 | Klicek ..................................... 606/37 |
| 5,540,684 | 7/1996 | Hassler, Jr. . |
| 5,556,396 * | 9/1996 | Cohen et al. .......................... 606/42 |
| 5,558,671 * | 9/1996 | Yates ..................................... 606/38 |
| 5,713,896 | 2/1998 | Nardella . |
| 5,722,975 * | 3/1998 | Edwards et al. ....................... 606/34 |
| 5,836,943 * | 11/1998 | Miller, III ............................. 606/34 |
| 5,954,717 * | 9/1999 | Behl et al. ............................. 606/34 |
| 5,971,980 * | 10/1999 | Sherman ............................... 606/34 |

* cited by examiner

*Primary Examiner*—Michael Peffley

(57) ABSTRACT

An electrosurgical generator has an output power control system that causes the impedance of tissue to rise and fall in a cyclic pattern until the tissue is desiccated. The advantage of the power control system is that thermal spread and charring are reduced. In addition, the power control system offers improved performance for electrosurgical vessel sealing and tissue welding. The output power is applied cyclically by a control system with tissue impedance feedback. The impedance of the tissue follows the cyclic pattern of the output power several times, depending on the state of the tissue, until the tissue becomes fully desiccated. High power is applied to cause the tissue to reach a high impedance, and then the power is reduced to allow the impedance to fall. Thermal energy is allowed to dissipate during the low power cycle. The control system is adaptive to tissue in the sense that output power is modulated in response to the impedance of the tissue.

19 Claims, 6 Drawing Sheets

ELECTROSURGICAL GENERATOR WITH ADAPTIVE POWER CONTROL

This application is a Continuation of U.S. application Ser. No. 08/838,548, filed on Apr. 9, 1997, now U.S. Pat. No. 6,033,399, the contents of which are incorporated herein by reference.

BACKGROUND

1. Field of the Invention

The present invention relates to an electrosurgical generator with an adaptive power control, and more particularly to an eleosurgical generator that controls the output power in a manner that causes impedance of tissue to rise and fall cyclically until the tissue is completely desiccated.

2. Background of the Disclosure

Electrosurgical generators are used by surgeons to cut and coagulate tissue of a patient. High frequency electrical power is produced by the electrosurgical generator and applied to the surgical site by an electrosurgical tool. Monopolar and bipolar configurations are common in electrosurgical procedures.

Electrosurgical generators are typically comprised of power supply circuits, front panel interface circuits, and RF output stage circuits. Many electrical designs for electrosurgical generators are known in the field. In certain electrosurgical generator designs, the RF output stage can be adjusted to control the RMS output power. The methods of controlling the RF output stage may comprise changing the duty cycle, or changing the amplitude of the driving signal to the RF output stage. The method of controlling the RF output stage is described herein as changing an input to the RF output stage.

Electrosurgical techniques have been used to seal small diameter blood vessels and vascular bundles. Another application of electrosurgical energy is tissue welding. In this application, two layers of tissue are grasped and clamped together while electrosurgical power is applied. The two layers are thereby welded together. Tissue welding is similar to vessel sealing, except that a vessel or duct is not necessarily sealed in this process. For example, tissue welding may be used instead of staples for surgical anastomosis. Electrosurgical power has a desiccating effect on tissue during tissue welding or vessel sealing. As used herein, the term "electrosurgical desiccation" is meant to encompass any tissue desiccation procedure, including standard electrosurgical coagulation, desiccation, vessel sealing, and tissue welding.

One of the problems associated with electrosurgical desiccation is undesirable tissue damage due to thermal effects. The tissue at the operative site is heated by the electrosurgical current. Healthy tissue adjacent to the operative site can become thermally damaged if too much heat is allowed to build up at the operative site. The heat may conduct to the adjacent tissue and cause a large region of tissue necrosis. This is known as thermal spread. The problem of thermal spread becomes important when electrosurgical tools are used in close proximity to delicate anatomical structures. Therefore, an electrosurgical generator that reduced the possibility of thermal spread would offer a better opportunity for a successful surgical outcome.

Another problem that is associated with electrosurgical desiccation is a buildup of eschar on the surgical tool. Eschar is a deposit on an electrosurgical tool that is created from tissue that is desiccated and then charred by heat. The surgical tools win often lose effectiveness when they are coated with eschar. The buildup of eschar could be reduced when less heat is developed at the operative site.

Practitioners have known that a measurement of electrical impedance of tissue is a good indication of the state of desiccation of the tissue. Several commercially available electrosurgical generators can automatically terminate output power based on a measurement of impedance. Several methods for determining the optimal point of desiccation are known in the field. One method sets a threshold impedance, and terminates power once the measured impedance of the tissue crosses the threshold. Another method terminates power based on dynamic variations in the impedance.

A discussion of the dynamic variations of impedance of tissue can be found in the article, Vallfors and Bergdahl "Automatically Controlled Bipolar Electrocoagulation," *Neurosurgical Review,* 7:2–3, pp. 187–190, 1984. FIG. 2 in the Vallfors article shows impedance as a function of time during heating of tissue. Valfors reports that the impedance value of tissue proved to be close to minimal at the moment of coagulation. Based on this observation, Vallfors suggests a micro-computer technique for monitoring the minimum impedance and subsequently terminating output power to avoid charring the tissue.

A second article by Bergdahl and Vallfors, "Studies on Coagulation and the Development of an Automatic Computerized Bipolar Coagulator," *Journal of Neurosurgery,* 75:1, 148–151, July 1991, discusses the impedance behavior of tissue and its application to electrosurgical vessel sealing. The Bergdahl article reported that the impedance had a minimum value at the moment of coagulation. The Bergdahl article also reported that it was not possible to coagulate safely arteries with a diameter larger than 2 to 2.5 millimeters. The present invention helps to overcome this limitation by enabling electrosurgical vessel sealing of larger diameter vessels.

U.S. Pat. No. 5,540,684 discloses a method and apparatus for electrosurgically treating tissue in a manner similar to the disclosures of Vallfors and Bergdahl. The '684 patent addresses the problem associated with turning off the RF output automatically after the tissue impedance has reached a minimum value. A storage device records maximum and minimum impedance values, and an algorithm computes an optimal time for terminating output power.

U.S. Pat. No. 4,191,188 discloses a variable crest factor electrosurgical generator. The crest factor is disclosed to be associated with the coagulation effectiveness of the electrosurgical waveform.

U.S. Pat. No. 5,472,443 discloses the variation of tissue impedance with temperature. The impedance of tissue is shown to fall, and then subsequently rise as the temperature is increased. The '443 patent shows a relatively lower temperature region (Region A in FIG. 2) where salts, contained within the body fluids, are believed to dissociate, thereby decreasing the electrical impedance. The relatively next higher temperature region (Region B) is where the water in the tissues boils away, causing the impedance to rise. The relatively highest region (Region C) is where the tissue becomes charred, resulting in a slight lowering of impedance.

It would be desirable to have an electrosurgical generator that produced a clinically effective output and, in addition, reduced the amount of heat and thermal spread at the operative site. It would also be desirable to have an electrosurgical generator that produced a better quality seal for vessel sealing and tissue welding operations. It would also be desirable to have an electrosurgical generator that desiccated tissue by applying a minimal amount of electrosurgical energy.

SUMMARY OF THE INVENTION

The present invention relates to an electrosurgical generator having an improved output power controller for increasing the quality and reliability of electrosurgically sealing vessels, sealing ducts, welding and desiccating tissue. In particular, the output power is controlled in a manner that causes impedance of tissue to rise and fall repeatedly until the tissue is completely desiccated. The output power and the tissue impedance are both part of a control system wherein the output power is cycled to thereby cause a cycling of the tissue impedance. A basis for this invention is an experimental observation that the electrical impedance of tissue will usually rise when electrosurgical power is applied, and the electrical impedance of tissue will usually fall when the electrosurgical power is reduced or terminated. Presently available electrosurgical generators will monitor the rising impedance of tissue as power is applied. However, the applicant is the first to design an electrosurgical generator with a power control system that actively cause the impedance of the tissue to rise and fall repeatedly until the tissue is desiccated, and thereby achieve beneficial surgical effects.

The application of electrosurgical power is known to cause the impedance of tissue to fall to a local minimum and then rise monotonically thereafter. If the electrosurgical power is applied for too long, the tissue may char and stick to the electrode. Whereas prior designs terminated output power after the first local minimum in the impedance measurement, the present invention actively causes several local impedance minima to occur. Power can be terminated in the present invention based on an impedance limit, a time limit, or based on the responsiveness of the tissue to changes in output power from the generator.

An advantage of the present invention is that it can coagulate tissue with a reduced level of tissue charring. Another benefit of the present invention is that it has improved tissue sealing characteristics. Yet another benefit of the present invention is that it reduces thermal spread and thereby reduces damage to adjacent tissue. Yet another advantage of the present invention is that it reduces the tendency for eschar buildup on the electrosurgical tool. Yet another advantage of the present invention is that large vessels and ducts can be electrosurgically sealed.

It is thought that impedance of tissue can rise and fall depending on several factors, including output power, output voltage, output current, temperature, and pressure on the tissue exerted by surgical graspers. The present invention addresses changes in impedance of tissue that can be attributed to electrosurgical power application, wherein the power can be adjusted by changing the output voltage or the output current. The present invention causes the tissue impedance to rise and fall repeatedly until the tissue is completely desiccated. The present invention adjusts the output power in a manner that is based on feedback from a tissue impedance measurement.

According to the present invention, the impedance of the tissue rises and falls in response to relatively low frequency cycling of the electrosurgical power. The electrosurgical power is raised and lowered (also referenced herein as "cycled") at a relatively low frequency, and the impedance of the tissue is thereby caused to rise and fall at approximately the same frequency until the tissue becomes desiccated. The manner in which the electrosurgical power is raised and lowered may be accomplished in several ways which incorporate well known principles of control system design.

The frequency of power cycling in the present invention is different from the RF modulation frequency of the electrosurgical waveforms, which are typically in the range of one hundred kilohertz to one megahertz. The frequency of power cycling of the present invention is also different from the duty cycle of generators that causes a coagulation effect on tissue, which is typically in the frequency range above one thousand hertz. The frequency range of power cycling in the present invention is typically between one and twenty hertz. Both the RF modulation and the duty cycling of present electrosurgical generators may occur simultaneously with the power cycling of the present invention.

The frequency at which the electrosurgical power is raised and lowered (i.e. cycled or modulated) should not be too high, otherwise the impedance of the tissue will not be able to rise and fall in response with an amplitude that will produce additional benefits. Similarly, the frequency should not be too low, otherwise the beneficial aspects of the invention will not become apparent because the tissue will desiccate without any appreciable modulation. The range of effective frequencies of the present invention has been called "thermal bandwidth."

The behavior of the tissue impedance is possibly related to the thermal time constant of the tissue. There are additional factors that affect the tissue impedance, including the water content in the tissue and steam. After the tissue is desiccated, which is indicated by a high measured impedance, further application of electrosurgical power will cause undesirable charring. Thus, it is preferred to have impedance monitoring to determine the appropriate time for terminating the electrosurgical power. Impedance monitoring is also preferred so that the modulation frequency of the electrosurgical power can be automatically adjusted and kept within the thermal bandwidth.

It is theorized by the inventor that thermal spread during electrosurgical desiccation is created in at least three ways. The first is through direct thermal conduction away from the weld site. The second is from hot steam exiting the weld site. This mechanism is perhaps far more significant than the first, because of the steam's high mobility. The third mechanism is the lateral spread of current away from the weld site. It is theorized that the third mechanism is due to steam creating a high impedance pathway between the jaws, which forces a larger portion of the current to flow laterally. The present invention controls the output power in a manner that reduces thermal spread.

The present invention is relevant to all electrosrgical generators. It has been found to be particularly relevant to bipolar electrosurgical applications, as well as to elecosurgical tissue welding and vessel sealing. Skilled practitioners will recognize the value of the invention wherever tissue desiccation is accomplished by electrosurgical methods.

DETAILED DESCRIPTION OF THE INVENTION

The present invention discloses an adaptive, oscillatory power curve which is able to reduce thermal spread in each of these areas by applying power in a cyclical fashion, rather than continuously. During the periods of reduced power application, thermal energy is allowed to dissipate which reduces direct thermal conduction. Also, the steam exits the weld site in smaller bursts, which produces less thermal damage than one large burst. Finally, the impedance between the jaws of the electrosurgical instrument is kept low, which allows current to flow more directly between the jaws.

Charring is also reduced. High voltages contribute to tissue charring, which is why it is preferable to limit the output voltage of the electrosurgical generator to 120 volts, and to periodically reduce it to a lower value during power cycling. A relatively low voltage is also important because it prevents electrical sparks, or arcs, from passing through the tissue and burning small holes in the newly sealed, or welded, tissue.

The transparency, or clarity, at the weld site has been identified as an indicator of successful seal completion. It also gives the surgeon visual feedback as to whether the seal is a success. Preliminary findings indicate that this method may also increase weld site transparency. The reason for this is unknown, but it seems reasonable that reduced charring will allow the weld site to remain more transparent.

Figure 1:
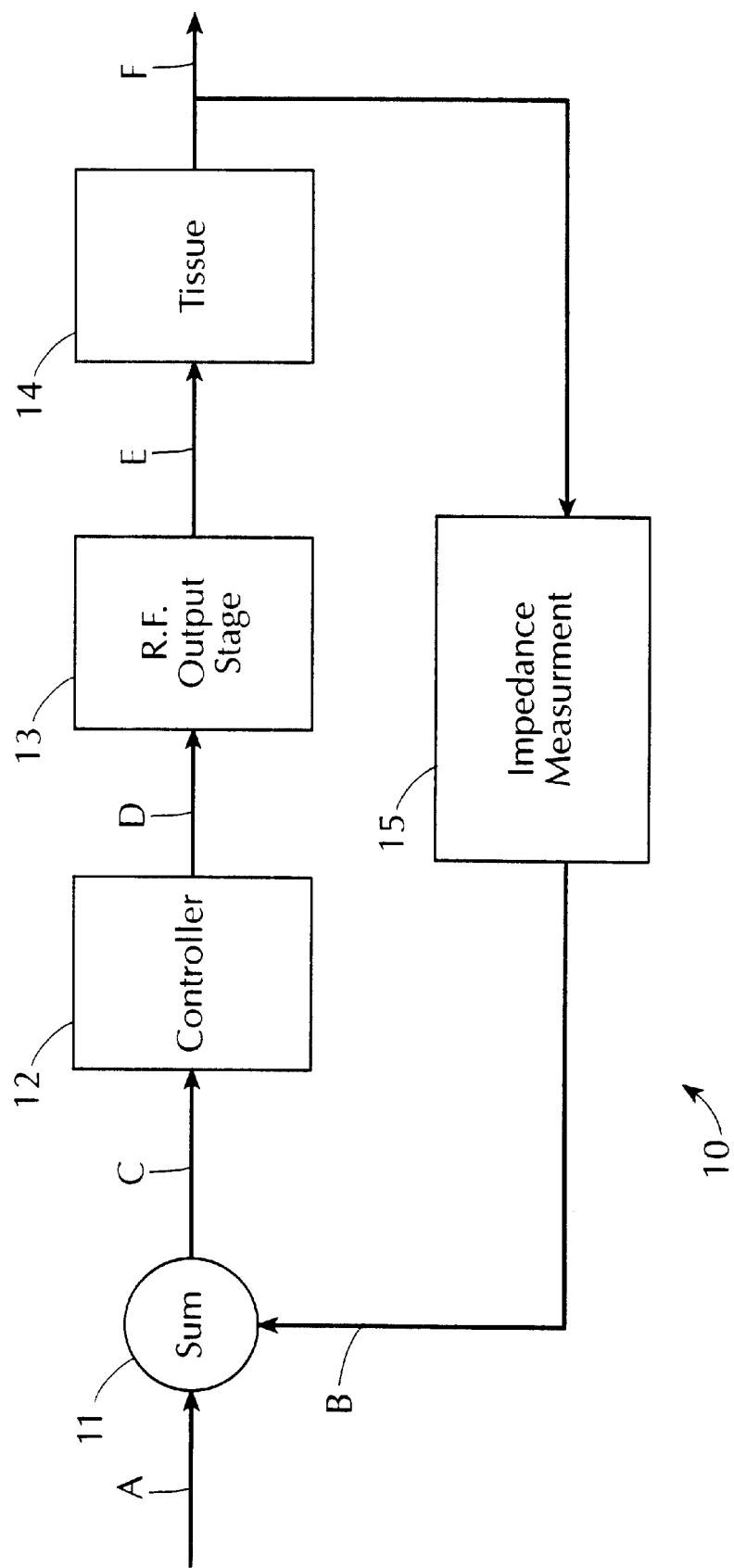
FIG. 1 is a block diagram representation of an adaptive oscillatory power curve according to the present invention.

Referring to FIG. 1, a block diagram of an adaptive oscillatory power control system 10 is shown. The line designated by the letter A represents the command input signal to the control system 10. The command input signal A is preferably a periodic function, and in stain embodiments the period may vary depending on the dynamics of the tissue. The signal A is representative of the desired tissue impedance. A measurement of tissue impedance is represented by line B. A summing block 11 compares the command input signal A with the measured tissue impedance B to produce a difference signal C. The summing block 11 may be comprised of an electrical comparator circuit as is commonly known to control systems engineers.

The difference signal C may be input to a controller 12 that generates a control signal D. The control signal D adjusts or terminates the output power of the electrosurgical generator by changing the state of the RF. Output Stage 13. The controller 12 may be comprised of an algorithm in a microprocessor that determines the conditions for power termination based on the amplitude of the control signal. Alternatively and equivalently, the controller 12 may be connected directly to the measured tissue impedance B to terminate power based on the amplitude of the measured tissue impedance B. The controller 12 may be comprised of any combination of proportional integral, and derivative control laws that are known to control system engineers. Other types of control laws, such as "bang-bang" control laws, are effective equivalents.

In one embodiment, the command input signal A has a cyclic pattern, for example a sine wave or a square wave. The cyclic nature of the command input signal A causes the control system 10 to regulate the output power in a cyclic manner to achieve beneficial surgical effects. The controller 12 monitors the difference signal C to determine the response of the output power E. In one embodiment, when the difference signal C is large, and the impedance measurement B is above threshold, then the controller 12 terminates the output power E.

The control signal D is preferably connected to an R.F. Output Stage 13. The control signal D preferably changes a driving voltage in the R.F. output stage to thereby change the RMS output power from the electrosurgical generator, shown as line E in FIG. 1. Alternatively and equivalently, the control signal D may change the duty cycle of the R.F. Output Stage 13 thereby effectively changing the RMS output power. Other means of changing RMS output power from an R.F. Output Stage, such as changing current, are known to electrical engineers.

The generator R.F. Output Stage 13 causes the electrosurgical generator to output a power level E to the tissue 14 of the patient. The tissue 14 becomes desiccated, thereby changing the electrical impedance, shown by F in FIG. 1. The electrical impedance F of the tissue is measured by an impedance measurement circuit 15 and reported as the measured tissue impedance B. The impedance measurement circuit 15 may be any form of electrical circuit that measures, or estimates, electrical impedance. The measured tissue impedance B is preferably an electrical signal that is proportional to the actual tissue impedance F.

Electrical engineers will recognize that output power from an electrosurgical generator can be adjusted in several ways. For example, the amplitude of the output power can be adjusted. In another example, the output power can be adjusted by changing the duty cycle or the crest factor. The change or adjustment in output power, as used herein is meant to refer any change or adjustment in the root mean square (RMS) value of the output power of the electrosurgical generator.

Figure 2A:
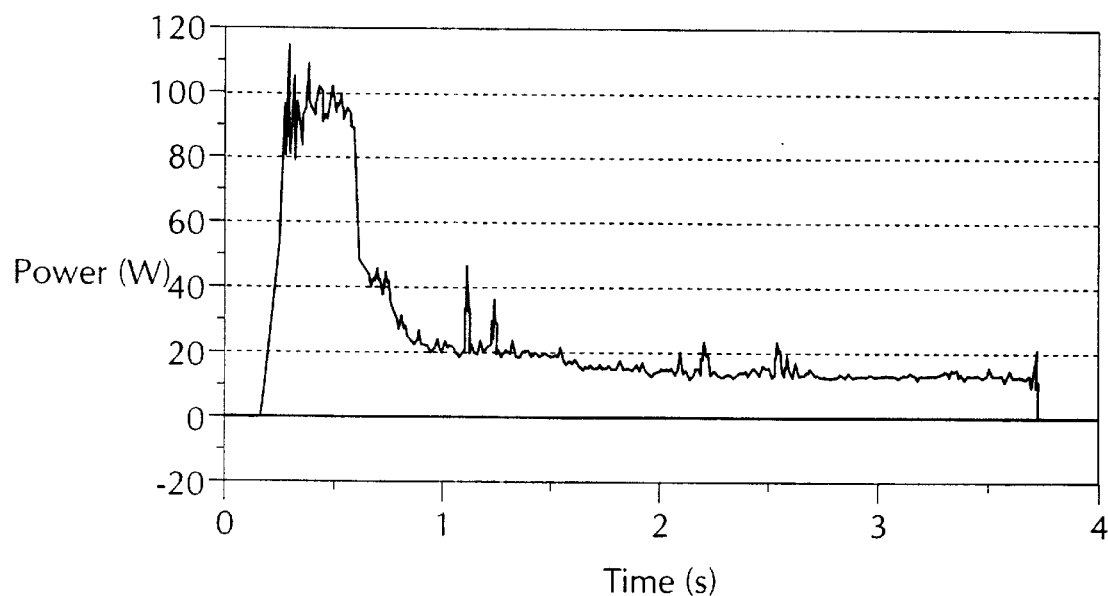
FIG. 2(a) is a sample of experimental data for a standard vessel sealing operation, showing output power as function of time.
Figure 2B:
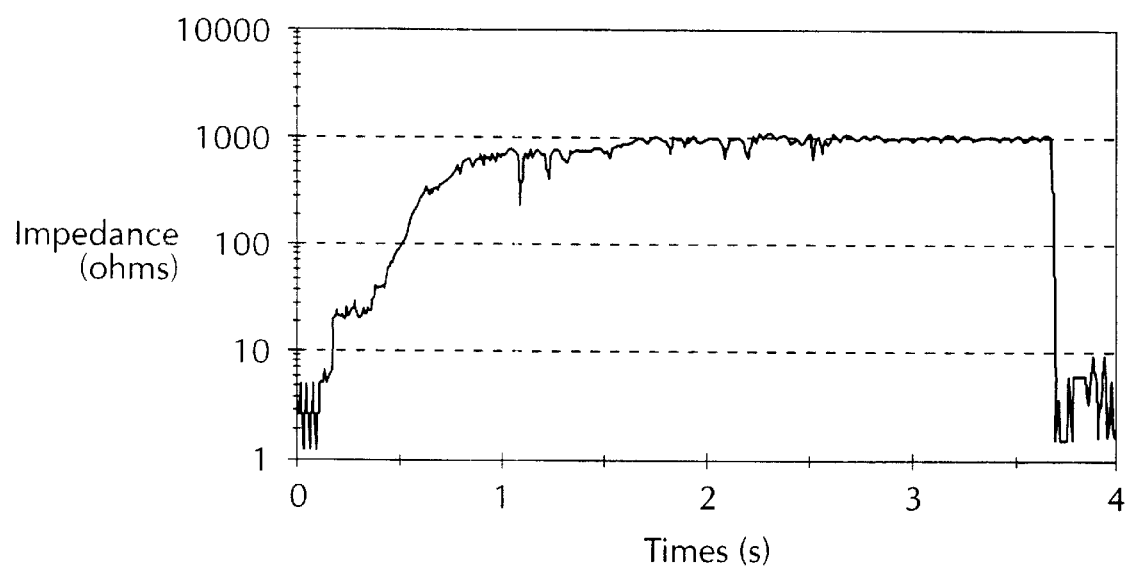
FIG. 2(b) is a sample of experimental data for a standard vessel sealing operation, showing load impedance as a function of time.
Figure 3A:
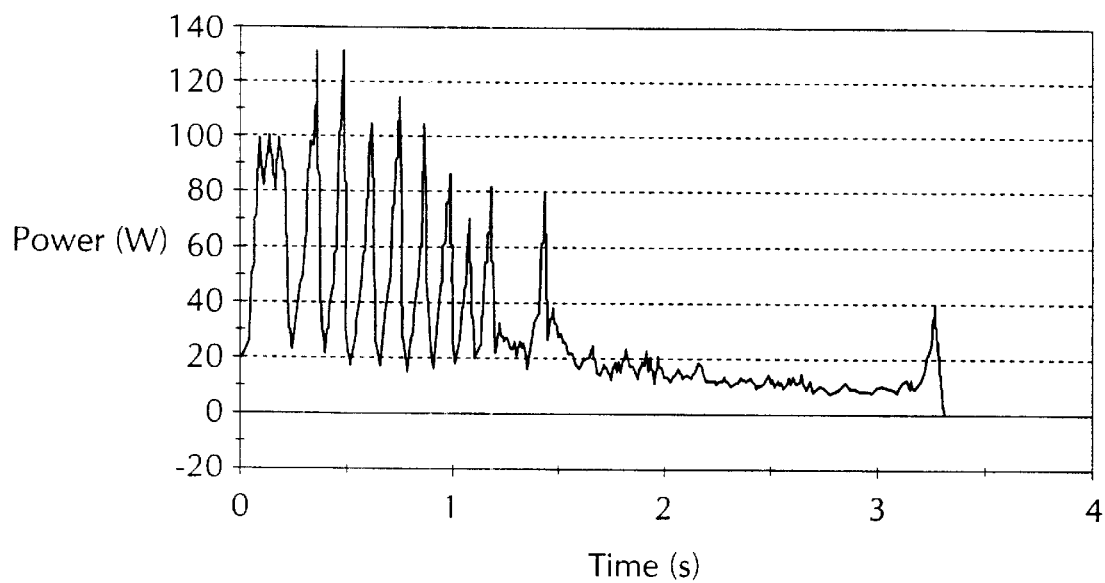
FIG. 3(a) is a sample of experimental data for an adaptive power control generator, showing output power as fiction of time.
Figure 3B:
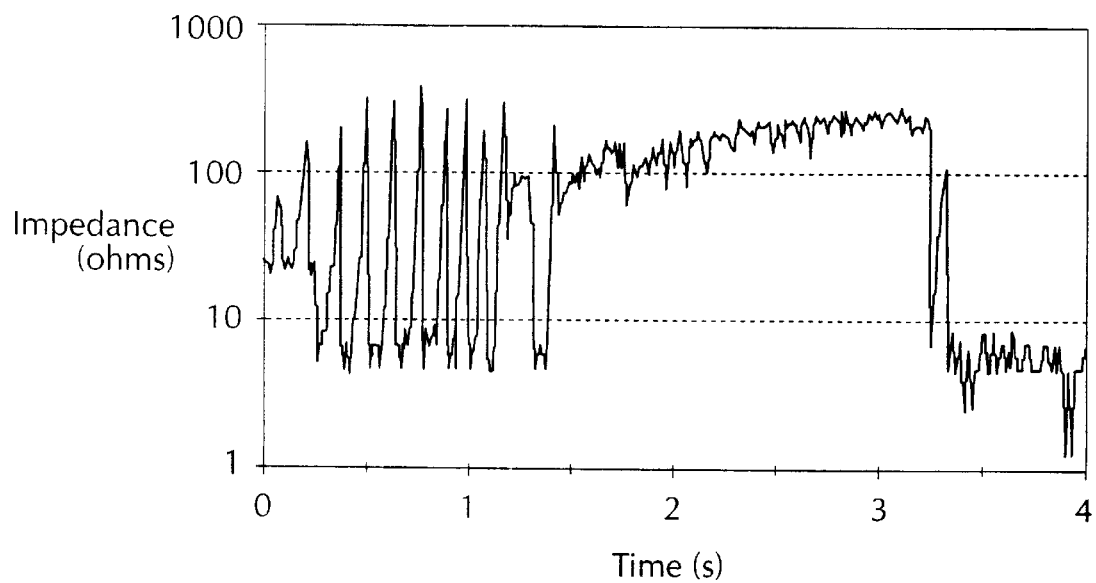
FIG. 3(b) is a sample of experimental data for an adaptive power control generator, showing load impedance as a function of time.

In operation, the control system 10 is designed to cycle the tissue impedance F for preferably several cycles in order to achieve beneficial effects. Thus, the command input signal A is a cyclically varying signal such as a sine wave. An example of cyclical impedance behavior of tissue is shown in FIG. 3(b). The generator output power that caused the cyclical impedance behavior is shown in FIG. 3(a). The cyclical behavior of the present invention can be contrasted with a standard electrosurgical generator wherein the output power is shown in FIG. 2(a) and the tissue impedance is shown in 2(b).

The present invention discloses an adaptive, oscillatory power curve which is able to reduce thermal spread in each of these areas by applying power in a cyclical fashion, rather than continuously. During the periods of reduced power application, thermal energy is allowed to dissipate which reduces direct thermal conduction. Also, the steam exits the weld site in smaller bursts, which produces less thermal damage than one large burst. Finally, the impedance between the jaws of the electrosurgical instrument is kept low, which allows current to flow more directly between the jaws.

Charring is thought to be reduced by the present invention. High voltages contribute to tissue charring, which is why it is preferable to limit the output voltage of the electrosurgical generator to 120 volts, and to periodically reduce it to a lower value during power cycling. A relatively low voltage is also important because it prevents electrical sparks, or arcs, from passing through the tissue and burning small holes in the newly sealed, or welded, tissue.

The transparency, or clarity, at the weld site has been identified as an indicator of successful seal completion. It also gives the surgeon visual feedback as to whether the seal is a success. Preliminary findings indicate that this method may also increase weld site transparency. The reason for this is unknown, but it seems reasonable that reduced charring will allow the weld site to remain more transparent.

Figure 4A:
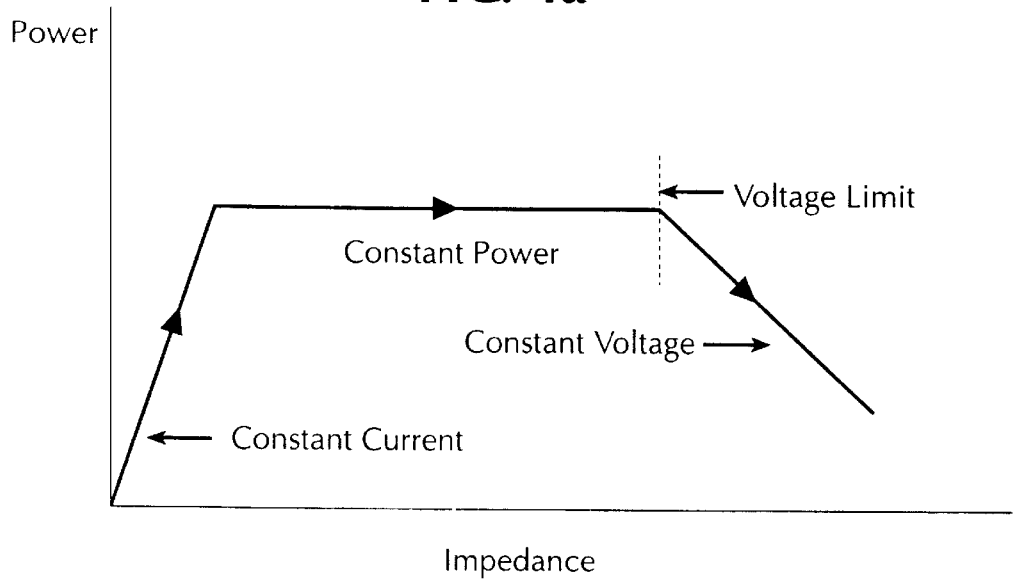
FIG. 4(a) is a representation of a power curve for a standard electrosurgical generator.

A plot of output power vs. load impedance is called a "power curve." A representation of a standard power curve is shown in FIG. 4(a). At low impedance, the output is typically current limited, and this is shown as the "constant current" line segment on FIG. 4(a). At midranges of impedance, the electrosurgical generator has a power control system that maintains the output power at a constant level by adjusting the output voltage, as shown by the "constant power" line segment on FIG. 4(a). Eventually, the load impedance becomes large, and the output power cannot be maintained without applying unacceptably high output voltages. Thus, a voltage limit is reached, and the output power drops off because the output current is falling and the output voltage is at a limit. The drop in output power is shown as the "constant voltage" line segment in FIG. 4(a).

Figure 4B:
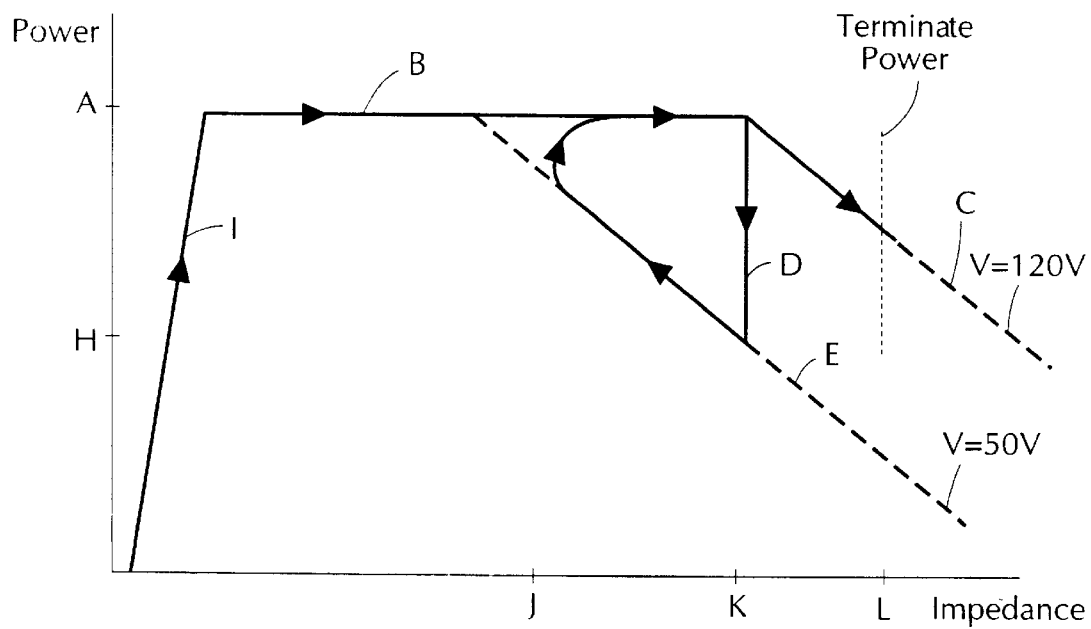
FIG. 4(b) is a representation of an adaptive oscillatory power curve.

The present invention is related to an electrosurgical generator having an adaptive oscillatory power curve as shown in FIG. 4(b). The adaptive oscillatory power curve is produced by a power control system in the electrosurgical generator. The design details of the control system can be implemented in several ways which are well known to control system engineers.

The first part of the adaptive oscillatory power curve, shown at the line segment I in FIG. 4(b), is similar to the standard power curve, wherein the generator applies high current into a low impedance load until a maximum power limit, shown as A, is reached. In the next "leg" of the power curve, shown by line segment B, output current begins to fall, and output voltage begins to rise as the generator adjusts the output voltage to maintain constant output power at the level marked by A. The generator then begins looking for signs to indicate the onset of boiling in the tissue. Such signs include a very rapid rise in impedance, or a high value of voltage, such as 120 volts. The local maximum of the impedance curve is shown by letter K in FIG. 4(b). The dotted line, marked C and labeled V=120 V, shows the possible output power if the generator were to maintain a voltage limit of 120 volts, which is a preferred voltage limit. Rather than follow the V=120 V line, a controller in the generator drops the output power. This can be accomplished, in one embodiment, by dropping the output voltage limit to between zero and 70 volts, and preferably 50 volts, as shown in line segment D. In another embodiment of the control system, the output power can be reduced by other combinations of output current reduction and/or output voltage reduction.

As a consequence of the lower voltage limit, the output power drops to the level indicated by H in FIG. 4(b). In certain embodiments, H may be zero watts. At this lower output power, desiccation stops and the tissue impedance starts to fall. A preferred lower voltage limit of 50 volts may be used as shown by dotted line E and marked "V=50 volts". Once the impedance has reached a local minimum, shown by J, or after a set period of time, the power control system raises the output power back to level A, which corresponds to an output voltage limit of 120 volts in the preferred embodiment. Thus, the output power rises back to level A, and the impedance rises again, until the onset of boiling or an impedance threshold is reached. The cyclical portion of the power curve incorporating line segments B, D, and E is an important part of this invention and will continue until the tissue is desiccated. When the tissue is desiccated, the power will terminate as shown when impedance reaches point L. In certain embodiments, point L will be substantially the same as point K.

The behavior shown in FIG. 4(b) can be observed in FIGS. 3(a), 3(b), 3(c) and 3(d). Power oscillations between 120 watts and 20 watts in FIG. 3(a) correspond to cyclical movement between power level A and power level H in FIG. 4(b). Impedance oscillations in FIG. 3(b) correspond to cyclical movement between impedance level K and impedance level J in FIG. 4(b). It will be understood by control systems engineers that FIG. 4(b) is highly idealized, and the cyclical behavior may not always reach exactly the same local maxima and minima. This can be observed in FIG. 3(a), where the local maxima of the power curve may not always reach 120 volts.

It is theorized by the inventor that the following phenomena occur. The initial high output power initiates boiling in the tissues. The subsequent low output power is insufficient to maintain boiling, and hence boiling in the tissue stops. After boiling stops, if the tissue is not completely desiccated then the impedance will fall to a lower value. Next, the low impedance allows output power to increase, which re-heats the tissue to the point of boiling. The voltage is also pulled higher during the process, and remains so until the power curve can sense the onset of boiling, and lower the voltage, preferably back to 50 volts. The process continues until the tissue is fully desiccated. An oscillation is one cycle of high output power followed by low output power.

FIGS. 2(a) through 2(d) show experimental results on tissue samples using a standard power curve. FIGS. 3(a) through 3(d) show experimental results using an adaptive oscillatory power curve. The general nature of the invention can be seen by comparing FIG. 2(a) with FIG. 3(a). FIG. 2(a) shows a 100 watt electrosurgical output that is applied continuously to tissue. As the tissue desiccates, the impedance of the tissue rises and the output power in FIG. 2(a) is seen to fall off below 20 watts. In contrast, FIG. 3(a) shows an oscillating output power that varies from approximately 100 watts to approximately 20 watts. The effects on tissue impedance can be seen by comparing FIG. 2(b) with FIG. 3(b). The tissue impedance resulting from the standard power curve is shown to continuously increase in FIG. 2(b), perhaps after an initial drop. The tissue impedance resulting from the adaptive oscillatory power curve is shown to oscillate in FIG. 3(b) and thus has several local minima.

Figure 2C:
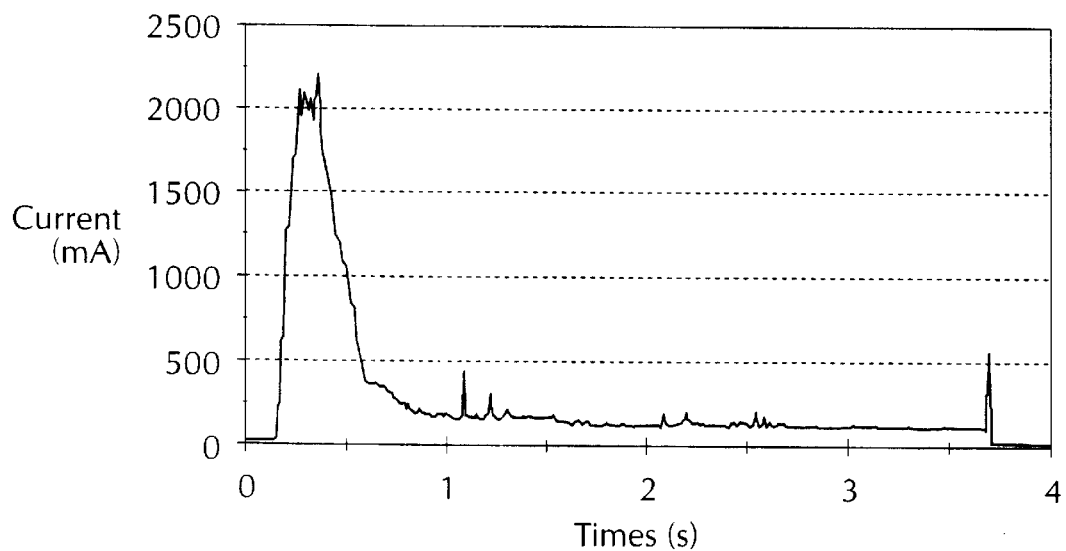
FIG. 2(c) is a sample of experimental data for a standard vessel sealing operation, showing output current as a function of time.
Figure 2D:
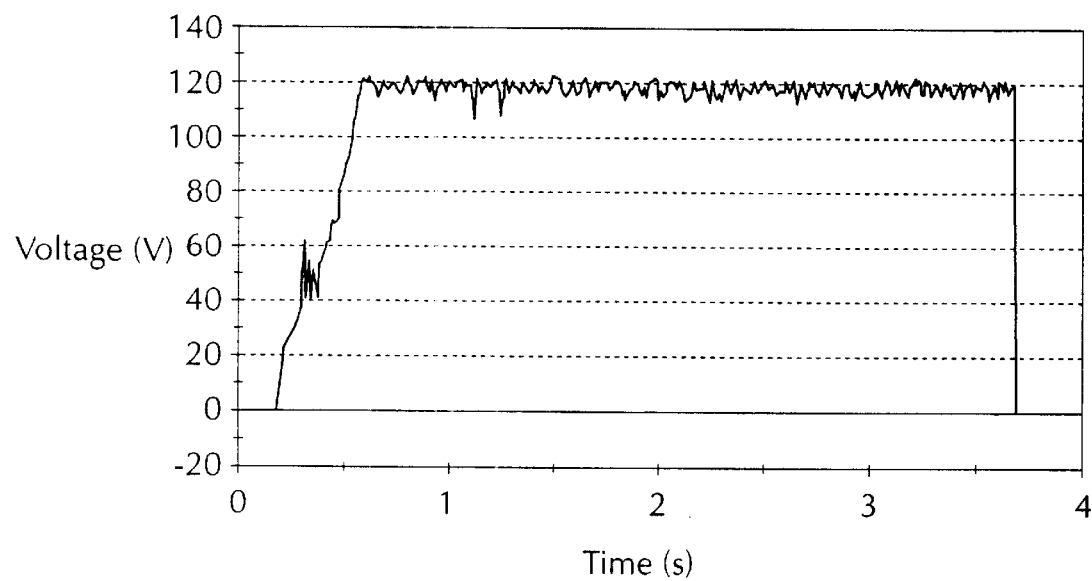
FIG. 2(d) is a sample of experimental data for a standard vessel sealing operation, showing output voltage as a function of time.
Figure 3C:
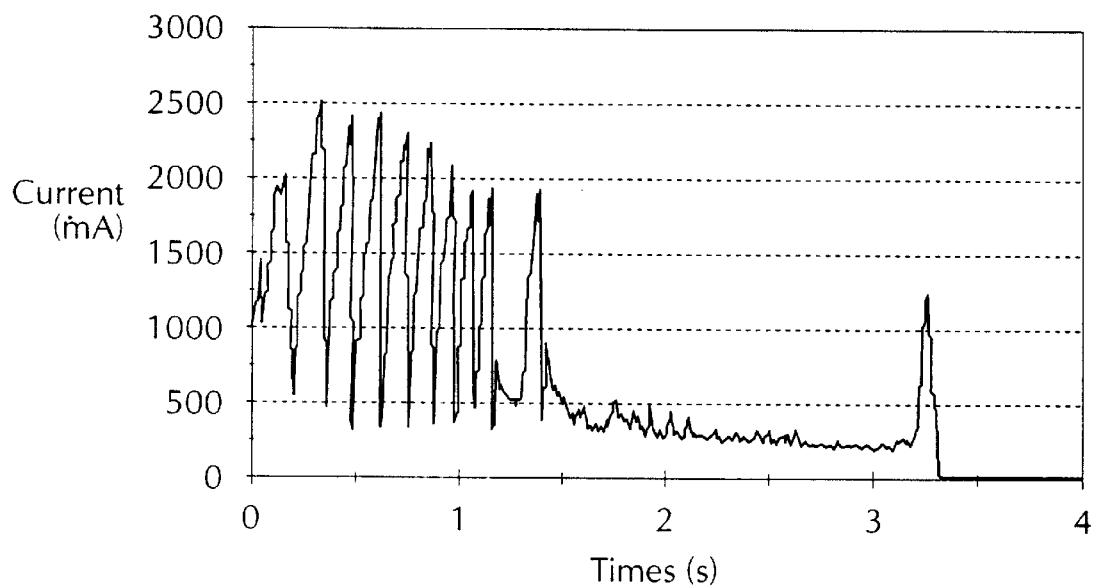
FIG. 3(c) is a sample of experimental data for an adaptive power control generator, showing output current as a function of time.
Figure 3D:
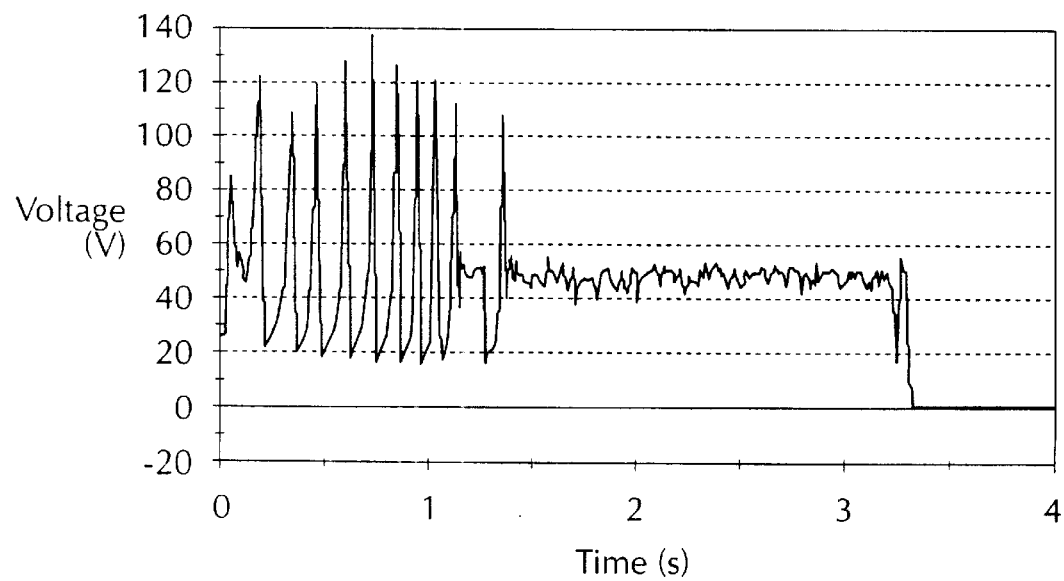
FIG. 3(d) is a sample of experimental data for an adaptive power control generator, showing output voltage as a function of time.

Output voltage and output current show a cyclic behavior in the adaptive oscillatory power curve. The cyclic behavior is absent in the standard power curve. FIGS. 2(c) and 3(c) can be compared to show the difference in output current between the standard power curve and the adaptive oscillatory power curve. In each case the maximum output current rises above 2 amps RMS. FIGS. 2(d) and 3(d) can be compared to show the difference in output voltage between the standard power curve and the adaptive oscillatory power curve. A voltage limit, preferably in each case 120 volts, prevents arcing that might leave pinholes in the tissue seal.

In one embodiment of the adaptive oscillatory power curve, the generator temporarily lowers the output voltage limit to 50 volts whenever the output voltage reaches 120 volts. This causes a reduction in output power, and if the tissue is not completely desiccated, a corresponding significant reduction in tissue impedance. After the reduction in tissue impedance, the output voltage limit is reset to 120 volts, allowing a rise in output power. This reduction and subsequent rise in output power constitutes a cycle.

Designers of electrosurgical generators have found that impedance is a good indicator of the desiccation state of the tissue. However, skilled artisans will recognize that it may not be necessary to compute an exact value for impedance. An electrical measurement that is proportional to the tissue impedance can be used as a functional equivalent. In one embodiment, the control system can properly create the adaptive oscillatory power curve based on measurements of time, and output voltage.

Table 1 shows a comparison between two sets of tests which compare a standard power curve with an adaptive oscillatory power curve. Test 1 indicates use of the standard power curve, while Test 2 indicates the use of the adaptive oscillatory power curve. Size indicates the vessel diameter in millimeters, burst pressures are measured in p.s.i., sticking, charring, and clarity are subjective measures ranked from 0 to 3, (where 0 represents a low value for sticking and charring, and 0 represents a poor value for clarity), and ts indicates thermal spread, measured in millimeters.

TABLE 1

Comparison of Standard Power Curve with Adaptive Power Curve

| Test | # samples | size | bp | stick | charring | clarity | ts |
|---|---|---|---|---|---|---|---|
| 1 (mean) | 19 | 2.57 | 17.26 | .63 | 1.11 | 1.89 | 2.11 |
| 1 (SD) | | 1.35 | 1.04 | .76 | .81 | 1.29 | .74 |
| 1 (min) | | 1 | 12.96 | | | | |
| 1 (max) | | 6 | 17.50 | | | | |
| 2 (mean) | 20 | 2.55 | 17.39 | .80 | .60 | 1.95 | 1.65 |
| 2 (SD) | | 1.36 | .44 | 1.06 | .60 | 1.36 | .81 |
| 2 (min) | | 1 | 15.52 | | | | |
| 2 (max) | | 5 | 17.50 | | | | |

Table 1 illustrates that the adaptive oscillatory power curve (Test 2) has several advantages over the standard power curve (Test 1). Most notable is the lower amount of thermal spread: a mean value of 2.1 mm for the standard power curve, and 1.65 mm for the adaptive oscillatory power curve. The subjective measures for sticking, charring and clarity of the weld show that the adaptive oscillatory power curve offer improvements over the standard power curve.

In general, the invention is an electrosurgical generator for treating tissue, wherein the electrosurgical generator comprises a circuit for generating a measurement of the load impedance, and an output power controller having means for inducing multiple oscillations of the load impedance in response to the measurement. The load impedance refers to the impedance of the tissue being treated by the electrosurgical generator. The circuit for generating a measurement of the load impedance can be analog or digital, and typically requires an output voltage sensor and an output current sensor. The output voltage is divided by the output current to compute a measurement of load impedance.

The means for inducing multiple oscillations of the load impedance preferably comprises a control system which can selectively control the output voltage to cause appropriate oscillations of the output power. In many electrosurgical generators, an output power control circuit has an adjustable voltage supply connected to the primary side of an isolation transformer. The secondary winding of the transformer is connected to an output resonant circuit. The voltage supply has an adjuster for changing the voltage to the transformer, and thereby changing the output voltage of the electrosurgical generator. A digital signal may be used to control the voltage supply.

The means for inducing multiple oscillations preferably comprise a feedback control system, where the feedback is a measurement of the load impedance. The control system preferably includes an algorithm in a microprocessor. The algorithm in the microprocessor can monitor the load impedance and determine how the load impedance is responding to a change in the output power.

In the preferred embodiment, the control system sets an output voltage limit of 120 volts RMS, and then controls the output power to a user desired setting, for example 100 watts. When the impedance is relatively low, a high current will combine with an output voltage of less than 120 volts to yield the desired power of 100 watts. As the impedance rises, the output current will fall, and the output voltage will be increased by the circuit to maintain the desired output power. When the voltage limit of 120 volts is reached, the control system will automatically lower the output voltage to a low value, preferably 50 volts. This effectively lowers the output power. If the tissue is not completely desiccated, the lower output power will cause the impedance to drop significantly. Once a local impedance minimum is detected, or after a set period of time, the output voltage limit is reset to 120 volts by the control system, and the cycle repeats. It has been found through experimentation that the oscillations of the load impedance will occur in the frequency range of one to twenty hertz, and this range has been referred to herein as the thermal bandwidth. In one embodiment, the control system terminates the output power after a set period of time which was three seconds. Alternatively, the control system can terminate power when the impedance reaches a threshold of 2000 ohms. Another alternative is to terminate output power when the measurement of impedance indicates that the impedance does not substantially fall in response to a drop in the output power.

The present invention is applicable to any form of electrosurgical coagulation. The benefits of the present invention, including reduced thermal spread, less eschar buildup, and improved desiccation, can be applied to both monopolar and bipolar electrosurgical generator outputs. While a particular preferred embodiment has been illustrated and described, the scope of protection sought is in the claims that follow.

What is claimed:

1. An electrosurgical generator for applying output power to tissue to desiccate tissue, the electrosurgical generator comprising:

a controller for cycling the output power to cause a cycling of the tissue impedance; and a tissue impedance measurement circuit coupled to said controller for measuring impedance of the tissue;

wherein the controller cycles the output power by applying a predetermined amount of output power to said tissue, lowering the output power upon an output voltage reaching a predetermined maximum, re-applying the predetermined amount of output power to said tissue if a measured tissue impedance does not indicate desiccation of the tissue, and terminating output power when the measured tissue impedance exceeds a predetermined value, the predetermined value corresponding to a desiccated condition of tissue.

2. The generator of claim 1, wherein the controller changes the output voltage to cycle the output power.

3. The generator of claim 1, wherein the controller changes the output current to cycle the output power.

4. The generator of claim 1, wherein the output voltage is cycled by lowering the output voltage once it reaches a predetermined maximum and raising the output voltage if the reduction in measured tissue impedance does not indicate desiccation of the tissue.

5. The generator of claim 1, wherein the output power is cycled at a frequency that is between 1 and 20 Hz.

6. The generator of claim 1, wherein the output voltage does not exceed 120 volts.

7. The generator of claim 1, further comprising a comparator wherein the measured tissue impedance value is compared to a first signal representative of a desired tissue impedance value by the comparator and a difference signal is produced.

8. The generator of claim 7, wherein the difference signal is input to the controller which generates a signal to adjust the power.

9. The generator of claim 7, wherein the first signal has a cyclic pattern.

10. The generator of claim 9, wherein the first signal is a sine wave.

11. An electrosurgical generator for treating tissue by applying energy comprising:
   a desiccation detector for measuring a degree of desiccation of tissue; and
   a controller for minimizing the burning of tissue comprising power control circuitry for repeatedly increasing and decreasing output power to the tissue to be treated, the power control circuitry coupled to the desiccation detector and operating to adjust the output power in response to the degree of desiccation of the tissue by applying a predetermined amount of output power to said tissue, lowering the output power upon an output voltage reaching a predetermined maximum, and re-applying the predetermined amount of output power to said tissue if said desiccation detector does not indicate desiccation of the tissue.

12. The generator of claim 11, wherein the output power is terminated by said controller upon detection of desiccated tissue.

13. The generator of claim 12, wherein the desiccation detector further comprises impedance measuring circuitry, wherein the degree of desiccation of the tissue is determined by the impedance of the tissue measured by the impedance measuring circuitry.

14. The generator of claim 13, wherein the circuitry adjusts the output power by adjusting the output voltage within a predetermined voltage range.

15. The generator of claim 11, wherein the output power is repeatedly increased and decreased by the circuitry at a frequency between 1 and 20 Hz.

16. A method for applying energy to tissue to treat tissue, the method including supplying a generator having a power control system to produce an adaptive oscillatory power curve to minimize the heating effect on tissue, the method comprising:
   a) applying a high current into a low impedance load until a maximum power is reached;
   b) adjusting the output voltage to maintain constant output power as impedance increases as tissue begins to desiccate;
   c) dropping the output power in response to a rapid rise in tissue impedance indicating the boiling of tissue;
   d) allowing the tissue impedance to fall to a predetermined minimum value and then raising the output power to cause an increase in tissue impedance;
   e) repeating steps b and c until impedance reaches a maximum value.

17. A method for applying energy to tissue to treat tissue, the method including supplying a generator having a power control system to produce an adaptive oscillatory power curve to minimize the heating effect on tissue, the method comprising:
   a) applying a high current into a low impedance load until a maximum power is reached;
   b) adjusting the output voltage to maintain constant output power as impedance increases as tissue begins to desiccate;
   c) dropping the output power if the output voltage exceeds a maximum value;
   d) raising the output power after a predetermined period of time to cause an increase in tissue impedance; and
   e) repeating steps b and c until impedance reaches a maximum value.

18. A method for applying energy to tissue to treat the tissue, comprising steps of:
   providing an electrosurgical generator;
   coupling an output of the generator to tissue to be treated; and
   coupling electrosurgical energy from the generator into the tissue in an oscillatory manner until an impedance of the tissue rises to a value that indicates that the tissue is desiccated, wherein the electrosurgical energy is coupled into the tissue with an oscillatory frequency that lies within a thermal bandwidth of the tissue.

19. A method as in claim 18, wherein the frequency is within a range of about one Hertz to about 20 Hertz.

* * * * *